United States Patent
Yamamoto et al.

(10) Patent No.: US 7,842,097 B2
(45) Date of Patent: *Nov. 30, 2010

(54) TISSUE REPAIR MATRIX

(75) Inventors: Ronald K. Yamamoto, San Francisco, CA (US); Michael K. Kwan, Cupertino, CA (US); Stephen D. Pacetti, San Jose, CA (US)

(73) Assignee: DePuy Spine, Inc., Raynham, MA (US)

( * ) Notice: Subject to any disclaimer, the term of this patent is extended or adjusted under 35 U.S.C. 154(b) by 852 days.

This patent is subject to a terminal disclaimer.

(21) Appl. No.: 10/856,981

(22) Filed: May 27, 2004
(Under 37 CFR 1.47)

(65) Prior Publication Data
US 2004/0220680 A1    Nov. 4, 2004

Related U.S. Application Data

(60) Division of application No. 10/086,225, filed on Feb. 22, 2002, now Pat. No. 6,764,517, and a continuation-in-part of application No. 09/782,794, filed on Feb. 13, 2001, now Pat. No. 6,902,584, which is a continuation of application No. 09/110,726, filed on Jul. 7, 1998, now Pat. No. 6,187,047, which is a division of application No. 08/633,554, filed on Apr. 17, 1996, now Pat. No. 5,776,193.

(60) Provisional application No. 60/005,523, filed on Oct. 16, 1995.

(51) Int. Cl.
 *A61F 2/28* (2006.01)
(52) U.S. Cl. .............. 623/23.51; 623/16.11; 623/23.61; 623/23.75; 424/423
(58) Field of Classification Search .......... None
See application file for complete search history.

(56) References Cited

U.S. PATENT DOCUMENTS

| | | | |
|---|---|---|---|
| 4,294,753 A | 10/1981 | Urist | |
| 4,434,094 A | 2/1984 | Seyedin et al. | |
| 4,440,750 A | 4/1984 | Glowacki et al. | |
| 4,455,256 A | 6/1984 | Urist | |
| 4,563,350 A | 1/1986 | Nathan et al. | |
| 4,627,982 A | 12/1986 | Seyedin et al. | |
| 4,698,326 A | 10/1987 | Sauk et al. | |
| 4,780,450 A | 10/1988 | Sauk et al. | |
| 4,789,663 A | 12/1988 | Wallace et al. | |
| 4,795,467 A | 1/1989 | Piez et al. | |
| 4,863,732 A | 9/1989 | Nathan et al. | |
| 4,888,366 A | 12/1989 | Chu et al. | |
| 4,962,091 A | 10/1990 | Eppstein et al. | |
| 5,092,883 A | 3/1992 | Eppley et al. | |
| 5,133,755 A | 7/1992 | Brekke | |
| 5,208,219 A | 5/1993 | Ogawa et al. | |
| 5,231,169 A | 7/1993 | Constantz et al. | |
| 5,236,456 A | 8/1993 | O'Leary et al. | |
| 5,264,214 A | 11/1993 | Rhee et al. | |
| 5,294,446 A | 3/1994 | Schlameus et al. | |
| 5,306,303 A | 4/1994 | Lynch | |
| 5,306,311 A | 4/1994 | Stone et al. | |
| 5,314,474 A | 5/1994 | Helms et al. | |
| 5,328,955 A | 7/1994 | Rhee et al. | |
| 5,338,772 A | 8/1994 | Bauer et al. | |
| 5,366,508 A | 11/1994 | Brekke | |
| 5,376,636 A | 12/1994 | Rutherford et al. | |
| 5,393,739 A | 2/1995 | Bentz et al. | |
| 5,397,770 A | 3/1995 | Levin et al. | |
| 5,413,989 A | 5/1995 | Ogawa et al. | |
| 5,425,770 A | 6/1995 | Piez et al. | |
| 5,531,794 A | 7/1996 | Takagi et al. | |
| 5,532,217 A | 7/1996 | Silver et al. | |
| 5,607,474 A | 3/1997 | Athanasiou et al. | |
| 5,645,591 A | 7/1997 | Kuberasampath | |
| 5,683,459 A | 11/1997 | Brekke | |
| 5,697,980 A | 12/1997 | Otani et al. | |
| 5,755,792 A | 5/1998 | Brekke | |
| 5,776,193 A | 7/1998 | Kwan | |
| 5,876,452 A | 3/1999 | Athanasiou et al. | |
| 6,013,853 A | 1/2000 | Athanasiou et al. | |
| 6,118,043 A | 9/2000 | Nies et al. | |
| 6,187,047 B1 | 2/2001 | Kwan et al. | |
| 6,764,517 B2 | 7/2004 | Yamamoto et al. | |
| 6,902,584 B2 | 6/2005 | Kwan et al. | |

FOREIGN PATENT DOCUMENTS

EP    0475077 A    3/1992

(Continued)

OTHER PUBLICATIONS

European Search Report from corresponding European Application No. 03709281.4 Issued Sep. 11, 2007.

(Continued)

*Primary Examiner*—David H Willse
*Assistant Examiner*—Javier G Blanco
(74) *Attorney, Agent, or Firm*—Weaver Austin Villeneuve & Sampson LLP

(57) ABSTRACT

A porous three-dimensional tissue repair matrix is provided which is biodegradable. The matrix is preferably formed from mineralized collagen where the mineral comprises particulate calcium phosphate immobilized in the matrix.

14 Claims, No Drawings

FOREIGN PATENT DOCUMENTS

| | | |
|---|---|---|
| EP | 0522569 | 1/1993 |
| GB | 1 271 763 | 4/1970 |
| JP | 07236688 | 9/1995 |
| JP | 4275732 | 6/2009 |
| WO | WO 89/04646 | 6/1989 |
| WO | WO 90/01955 | 3/1990 |
| WO | WO 90/10018 | 9/1990 |
| WO | WO 91/18558 | 12/1991 |
| WO | WO 92/20371 | 11/1992 |
| WO | WO 93/04710 | 3/1993 |
| WO | WO 93/05808 | 4/1993 |
| WO | WO 93/05823 | 4/1993 |
| WO | WO 94/00145 | 1/1994 |
| WO | WO 9401483 | 1/1994 |
| WO | WO 94/15653 | 7/1994 |
| WO | WO 95/08304 | 3/1995 |
| WO | WO 9508304 A1 * | 3/1995 |
| WO | WO 97/14376 | 4/1997 |

OTHER PUBLICATIONS

European Search Report from corresponding European Application No. 03709281.4 Issued Nov. 6, 2006.

Urist, Marshall; Bone: Formation by autoinduction:, Science 12, vol. 150, No. 3698, pp. 893-899, Nov. 1965.

Reddi, et al., "Introduction and Maintenance of New Bone Formation by Growth and Differentiation Factors", Annales Chirurgiae et Gynacologiae, vol. 77, pp. 189-192, 1998.

Wiltfant, et al., "Ectopic Bone Formation with the help of Growth Factor bFGF", Journal of Cranio-Maxxillofacial Surgery, vol. 24, No. 5, pp. 300-304, Oct. 1996.

Wozney, "Bone Morphogenetic Proteins" Progress in Growth Factor Research, vol. 1, pp. 267-280, 1989.

Wang, JS, Aspenburg P., "Basic Fibroblast Growth Factor Increases", Allograft Incorporation; Acta Orthopaedica Scandinavica, vol. 65, No. 1, Feb. 1994, pp. 27-31.

Wang, JS, et al., "Basic Fibroblast Growth Factor Enhances bone-graft incorporation: Does and time Dependence in Rats", , Journal of Orthopaedic Research, US, The Journal of Bone and Joint Surgery, Inc., vol. 14, No. 2, Mar. 1996, pp. 316-323.

Mayahara, H. et al., "In Vivo Stimulation of Endosteal Bone formation by Basic Fibroblast Growth Factor In Rats", Growth Factors, vol. 9, 1993, pp. 73-80.

Taiho, Yuukuhin Kogyo KK, Patent Abstracts of Japan, JP 02 000213A; Mar. 8, 1990, vol. 014, No. 123 (C-0698),Jan. 5, 1990.

Denki Kagaku Kogyo KK, Patent Abstracts of Japan, JP 04282322A, Feb. 19, 1993, vol. 17, No. 086 (C-1028), Oct. 7, 1992.

Examination Report dated Oct. 12, 2004, for related New Zealand Application No. 535466.

U.S. Appl. No. 09/782,794, Yamamoto et al.

Chinese Office Action from corresponding China Application No. 03808980.7 Issued Jun. 13, 2008.

Japanese Official Action dated Oct. 27, 2008 for related Japanese Patent Application No. 9-515932.

European Examination Report dated Nov. 7, 2008 for related European Patent Application No. 03709281.4.

Third Office Action dated Jan. 23, 2009 for related Chinese Patent Application No. 03808980.7.

Inquiry from corresponding Japanese Application No. 9-515932 dated Apr. 30, 2008.

Office Action dated May 22, 2009 for Chinese Patent Application No. 03808980.7.

Office Action dated Sep. 28, 2009 for Japanese Patent Application No. 2003-570739.

Office Action dated Oct. 15, 2009 for Japanese Patent Application No. 2006-272877.

Office Action dated Dec. 29, 2009 for Canadian Patent Application No. 2,476,929.

Shanbhag et al., "Macrophage/particle interactions: effect of size, composition and surface area", J Biomed Mater Res., Jan. 1994, 28(1): 81-90.

Final Rejection received Aug. 3, 2010 for Japanese Patent Application No. 2003-570739.

* cited by examiner

TISSUE REPAIR MATRIX

CROSS REFERENCE TO RELATED APPLICATIONS

This application is a divisional of prior application Ser. No. 10/086,225, filed Feb. 22, 2002, now U.S. Pat. No. 6,764,517, which claims priority to provisional application Ser. No. 60/005,523, filed Oct. 16, 1995. This is a continuation-in-part of application Ser. No. 09/782,794, filed Feb. 13, 2001, now U.S. Pat. No. 6,902,584, which is a continuation of application Ser. No. 09/110,726, filed Jul. 7, 1998, now U.S. Pat. No. 6,187,047; which is a divisional of application Ser. No. 08/633,554, filed Apr. 17, 1996, now U.S. Pat. No. 5,776,193, all of which are incorporated by reference herein.

BACKGROUND

The invention relates to materials useful for bone tissue repair.

There have been a number of materials studied to initiate bone repair and/or to restore or replace missing bone to address the problem of stimulating formation of bone at specific sites.

Among the approaches used to address this problem is a conformational method whereby an implant material, usually made of metal ceramic or other inorganic material in a form intended to mimic the form of the missing bone, is inserted into the site in which bone replacement is required. There is a risk that the host will reject the material or there will be a failure of integration of the implant with normal skeletal tissue. Some ceramic materials such as ceramic tricalcium phosphate, although acceptably biocompatible with the host and bone, when used as an implant, appear to lack sufficient mechanical properties of bone for general utility and the bone does not consistently grow into and become incorporated within the implant.

Another approach involves substituting the missing bone tissue with a matrix which functions as a support into which the new bone growth can occur. The theory is that the matrix attracts the cells committed to an osteogenic pathway and the new bone grows in and through the matrix by the process referred to as osteoconduction. Allogeneic bone (non-host bone) grafts are used for this method, however there is a substantially high failure rate. Even when the allogeneic bone grafts are accepted by the host, healing periods for consolidation and capacity for mechanical stress are of comparatively long duration compared to autogeneic bone (host-bone) grafting. The use of allogeneic bone also presents the issue of transmissible viral agents.

A third method involves the process known as osteoinduction, which occurs when a material induces the growth of new bone from the host's undifferentiated cells or tissues, usually around a temporary matrix. A number of compounds are shown to have such a capacity. See for example, U.S. Pat. Nos. 4,440,750 to Glowacki, 4,294,753 and 4,455,256 to Urist and 4,434,094 and 4,627,982 to Seyedin et al. The most effective of these compounds appear to be proteins which stimulate osteogenesis. However, when synthesized from natural sources they are present in extremely low concentrations and require large amounts of starting material to obtain even a minute amount of material for experimentation. The availability of such proteins by recombinant methods may eventually make the use of such proteins per se of more practical value. However, such proteins will probably still need to be delivered to the desired site in an appropriate matrix.

There have been compositions disclosed containing collagen and various forms of calcium phosphate directed to healing and bone growth.

U.S. Pat. No. 5,338,772 to Bauer et al. discloses a composite material containing calcium phosphate ceramic particles and a bio-absorbable polymer where the calcium phosphate ceramic is at least 50% by weight and the particles are joined by polymer bridges. The calcium phosphate ceramic particles are disclosed as having a size of about 20 microns to about 5 mm.

U.S. Pat. No. 4,795,467 to Piez et al. discloses a composition comprising calcium phosphate mineral particles admixed with atelopeptide reconstituted fibrillar collagen. The calcium phosphate mineral particles are disclosed as having a size in the range of 100-2,000 microns.

U.S. Pat. No. 4,780,450 to Sauk et al. discloses a composition for bone repair comprising particulate polycrystalline calcium phosphate ceramic, a phosphophorin calcium salt and a type I collagen in a weight ratio of 775-15:3-0.1:1. The ceramic particles are disclosed as being dense hydroxyapatite about 1 to 10 microns in diameter or larger dense hydroxy apatite ceramic particles of greater than about 100 microns in diameter.

PCT Application WO 94/15653 to Ammann et al. discloses formulations comprising tricalcium phosphate (TCP), TGF-β and, optionally, collagen. The TCP is disclosed as being a delivery vehicle for the TGF-β, such that the TCP is of the particle size greater than 5 microns and preferably greater than about 75 microns. The most preferred range for the size of the TCP granules is disclosed as being 125-250 microns.

PCT Application WO 95/08304 discloses polymineralic precursor particles of hydroxyapatite mixed with insoluble collagen. The particle size of the polymineralic precursor particles are in the range from 0.5 microns to 5 microns. The precursor minerals are converted to hydroxyapatite by hydrolysis, and this process, it is believed, fuses the mineral to form monolithic hydroxyapatite.

British Patent Specification 1,271,763 to FMC Corporation discloses complexes of calcium phosphate and collagen.

SUMMARY OF THE INVENTION

A tissue repair matrix is provided which is porous, biodegradable, three-dimensionally fixed and has shape memory and maintains structural integrity and porosity after implant for a period sufficient to augment the tissue replacement process. The matrix comprises mineralized fibrillar insoluble collagen, collagen derivative or modified gelatin, bound with a binder. In one embodiment, the minerals comprise calcium phosphate immobilized within the matrix. The resulting product is lyophilized, cross-linked, dried and sterilized to form a porous matrix. The matrix may be used as a tissue repair material and/or a delivery vehicle for biologically active factor. The matrix may be implanted for bone regeneration and will retain its porosity and physical integrity for a period of greater than fourteen days after implant.

DESCRIPTION OF THE SPECIFIC EMBODIMENTS

The matrix is produced using a water-insoluble biodegradable biopolymer such as collagen, collagen derivative or modified gelatin. If gelatin is used, it will be modified to be insoluble in aqueous environments. The collagen may come from mineralized or unmineralized collagen sources, usually unmineralized collagen sources. Thus, the collagen may come from bone, tendons, skin, or the like, preferably Type I collagen which involves a combination of two strands of $\alpha_2$ and one $\alpha_1$ collagen chains. The collagen may be from a young source, e.g., calf, or a mature source, e.g., cow of two or more years. The source of the collagen may be any convenient animal source, mammalian or avian, and may include bovine, porcine, equine, chicken, turkey, or other domestic source of collagen. The insoluble collagenous tissue which is employed will normally be dispersed in a medium at an elevated pH, using at least about pH 8, more usually about pH 11-12. Commonly, sodium hydroxide is employed, although other hydroxides may be used, such as other alkali metal hydroxides or ammonium hydroxide.

Native collagen may be utilized in accordance with the present invention. Native collagen contains regions at each end which do not have the triplet glycine sequence. These regions (the telopeptides) are thought to be responsible for the immunogenicity associated with most collagen preparations. The immunogenicity can be mitigated by the removal of these regions to produce atelopeptide-collagen by digestion with proteolytic enzymes, such as trypsin and pepsin.

The concentration of collagen for mineralization will generally be in the range of about 0.1 to 10 weight percent, more usually from about 1 to 5 weight percent. The collagen medium will generally be at a concentration of the base in the range of about 0.0001 to 0.1N. The pH is generally maintained during the course of the reaction in the range of about 10-13, preferably about 12.

Insoluble, fibrillar collagen is preferably used and can be prepared by routine methods. Typically, this can be accomplished with by first mixing with isopropanol (IPA), diethyl ether, hexane, ethyl acetate, or other suitable solvent, and separating the collagen. The pH is typically lowered to about 3, then cooled to about 4° C., and allowed to swell. The resulting slurry may be homogenized until the desired viscosity is attained.

The homogenized slurry is mixed with solvent, agitated, and the pH is raised to about 7. The fibrillar collagen is separated, rinsed with deionized water, and lyophilized. To produce mineralized fibrillar collagen, the purified insoluble collagen fibrils may be homogenized, placed in a reactor where calcium chloride (typically, 0.05 m) and tribasic sodium phosphate (typically, 0.03 m) are introduced at a controlled rate with stirring. Sodium hydroxide is used to adjust pH at 11.0±0.5 as needed during this process. After mineralization, the collagen is rinsed with deionized water or phosphate buffer, combined with the binder and the pH is adjusted within a range of 8.0±2.0. A method of addition of phosphate and calcium ions is described in U.S. Pat. No. 5,231,169.

The calcium phosphate may contain other ions, such as carbonate, chloride, fluoride, sodium or ammonium. The presence of carbonate results in a product having the properties of dahllite (carbonated hydroxyapatite), while fluoride provides a product having the properties of fluoridated apatite. The weight % of carbonate will usually not exceed 10, while the weight of % of fluoride will usually not exceed 2. preferably in the range of 0 to 1. These ions may be present in conjunction with the calcium and/or phosphate source, so long as the ions are compatible and do not result in precipitation in the reagent solutions.

The rate of addition of the calcium and phosphate ions is generally about one hour and no more than about 72 hours in order to achieve the particle size of about 5 microns or less. Generally, the addition period is in the range of about 2 to 18 hours, more usually, in the range of about 4 to 16 hours. Mild temperatures are employed, usually not more than about 40° C., preferably in the range of about 15° to 30° C. The weight ratio of the collagen to calcium phosphate mineral will generally be in the range of about 20:1 to 1:1, and typically will be about 7:3.

Other additives such as, non-collagenous proteins, factors or drugs, such as BMP's, TGF-$\beta$, calcitonin, antibiotics may be included in the matrix by adding to the collagen slurry, prior or subsequent to calcium and phosphate addition. The amounts of such additives will generally be in the range of about 0.0001 to 2 weight % based on the biopolymer used as the matrix, such as collagen.

The amount of collagen present in the mineralized product will generally be from about 95% to 30%, based on the weight of collagen fibers exclusive of the binder.

To form a porous, three-dimensionally fixed tissue repair matrix having shape memory, the mineralized biopolymer fibers are mixed with a binder.

Preferably, purified soluble collagen is used as the binder by first mixing soluble collagen with a solvent, such as isopropanol (IPA), and isolating the collagen. The pH is lowered to about 3.0, then, when the collagen is dissolved, the pH is raised to 5.0 washed twice with the solvent, rinsed with deionized water, sieved, and lyophilized.

Other binders which may be used include, but are not limited to, gelatin, polylactic acid, polyglycolic acid, copolymers of lactic and glycolic acid, polycaprolactone, carboxymethylcellulose, cellulose esters (such as the methyl and ethyl esters), cellulose acetate, dextrose, dextran, chitosan, hyaluronic acid, ficol, chondroitin sulfate, polyvinyl alcohol, polyacrylic acid, polypropylene glycol, polyethylene glycol, water soluble methacrylate or acrylate polymers.

To prepare the porous matrix, the preferred soluble collagen binder is added to a mineralized biopolymer slurry and blended. Preferably, insoluble collagen is the biopolymer and a proportion of about 10% (wt:wt) soluble to insoluble collagen is used. The pH is adjusted to 8.0±2.0, as needed. When the desired level of blending is achieved, the dispersion is frozen at −20° C. to −80° C.

The frozen slurry is lyophilized. The porous matrix may be cross-linked to enhance physical stability, increase the resorption time of the matrix and ease the handling of the final product. The lyophilized matrix is preferably cross-linked using glutaraldehyde in solution (typically, 0.01%) or vapor. If a solution is used, after removal of excess reagent, the matrix is dehydrated by lyophilization.

The porous matrix may also be formed by filtering the slurry of mineralized collagen fibers and binder to form a web. The dried web may then be cross-linked.

The porous structure may also be achieved by mixing the biopolymer collagen fibers, binder and leachable particles (soluble salts, such as sodium chloride) and/or high vapor pressure solids which can be later removed by sublimation. The slurry can be dried, then the leachable or sublimable particles can be removed to form the porous structure. The porous matrix may be cross-linked.

Other benefits of a cross-linked matrix include greater implant residence time and shape retention (no fragmentation of the implant). The matrix has a shape memory, meaning that it is compressible from its initial size, shape and porosity and can return from a compressed state to its initial size, shape and porosity. Moreover, this can occur without substantial loss of its fibers or binder. The matrix will also maintain its porosity in physical integrity after implantation for greater than about fourteen days particularly when used for bone growth.

Other cross-linking methods and agents may be used, such as formaldehyde, chromium salts, di-isocyanates, carbodiimides, difunctional acid chlorides, difunctional anhydrides, difunctional succinimides, dibromoisopropanol, epichlorohydrin, diepoxides, dehydrothermal cross-linking, UV radiation when dry, or E-beam or gamma radiation in aqueous solution.

Final product sterilization may be accomplished using gamma radiation, E-beam radiation, dry heat or ethylene oxide.

An advantage of the present invention is that the collagen fibrils and the immobilized calcium phosphate mineral form a matrix particularly advantageous for the replacement or augmentation of bone. The matrix maintains its physical integrity and its porosity for a period of greater than about fourteen days after implant into a physiological environment in the case of bone replacement. By physical integrity it is meant that the matrix also maintains its porosity which is important to the tissue replacement or augmentation process. The matrix also has shape memory as described above. This is advantageous in that the matrix can be compressed into a delivery vehicle such as a cannula and the delivery vehicle can be introduced at the site of desired tissue growth. By releasing the matrix from the delivery vehicle at the site, the matrix returns to its initial size, shape and porosity without substantial loss of its fibers and binder. This is in contrast to compositions which, immediately or shortly after implant, collapse into an amorphous, non-porous mass and lose the mineral.

The matrix according to the present invention will eventually biodegrade or be resorbed, so the porosity and physical integrity cannot be maintained beyond that limiting period. This process normally takes on average, over about 2 to 12 weeks, and is of course dependent upon the size of the matrix that is implanted. However, as long as the period after which there has been complete absorption or biodegradation of the matrix has not occurred prior to the bone replacement or augmentation process, the rate of biodegradation will be sufficient.

It is an aspect of the present invention that the calcium phosphate minerals, typically present as hydroxyapatite, are immobilized on the matrix, as opposed to being freely mobile throughout the matrix. It has been found that the calcium phosphate mineral according to the present invention is immobilized within the matrix. The cellular response can be altered in that phagocytic cells such as giant cells and macrophages are more prominent around particulate materials, frequently forming granulomas. Particles small enough to be phagocytized, approximately 3 to 5 microns or less in size, are taken up by phagocytic cells which further stimulate a localized tissue reaction. For example, it is observed during bone healing that particulate wear debris associated with artificial joints are found in the macrophages of adjacent tissue and is associated with increased bone resorption in animal models in a dose dependent manner ("Macrophage/particle interactions: effect of size, composition, and surface area", Shanbhag A S et al., J. Biomed. Mater. Res. 28(1), 81-90 (1994)). It is thus an advantage of the invention that the immobilized calcium phosphate mineral is released over time as 5 micron or less particles, an ideal size to be taken up by phagocytic cells. It is a further advantage of the invention that any release of the calcium phosphate mineral particles is controlled, which is a result of mineral being immobilized within the matrix. The advantages of the particle size and immobilization are shown in Example III, below.

The matrix material has application as a tissue or cartilage repair, or osteoconductive bone grafting material for spinal fusion, filling bone defects, fracture repair and grafting periodontal defects. By combining the subject composition with an osteogenic material, such as autogenous bone or autologous aspirated bone marrow, or osteoinductive bone growth factors, BMP's, calcitonin or other growth factors, bone induction and growth may be further augmented. The subject composition may also contain other additives such as drugs, and in particular antibiotics. The matrix may also provide a substrate to which growth factors may bind, so that factors produced by the host or externally introduced can concentrate at the matrix. The subject compositions find application in tissue or cartilage repair, fracture repair, maxifacial reconstruction, spinal fusion, joint reconstruction, and other orthopedic surgical uses.

The following examples are provided by way of illustration and are not intended to limit the invention in any way.

Example I

Implanation in Bone

The mineralized collagen matrix according to the invention is implanted into defects created in the parietal bones of 8 week-old rats. Histological assessments are performed at 14 and 28 days. After 14 days, bone growth from the cut edge of the defect into the collagen matrix is observed. The newly formed woven bone surrounds pieces of the residual matrix and areas of loose connective tissue in which vascularization is evident. By 28 days, significant remodeling had occurred, with osteocytes present throughout the new bone. The connective tissue cavities seen at 14 days diminished in size as bone growth continued.

Example II

Implanation in Bone with Marrow or Autogenous Graft

The calcium phosphate mineralized collagen matrix from Example I was implanted with the addition of bone marrow into mature male New Zealand white rabbits (3.7 to 4.1 kilograms). An incision was made mid-shaft over the anterior-medial surface of the right forearm to expose the radius. A critical defect was created by removing a 1.5 centimeter segment of the radius using a pneumatic drill. Irrigation was provided during osteotomy to minimize overheating and damage to the bone. The defect was filled with the mineralized collagen matrix mixed with bone marrow or autogenous graft. The bone marrow was aspirated from the tibia of the same animal. The autogenous graft was cancellous bone harvested from the iliac crest similar to the current bone augmentation or grafting procedure. Post-surgically, the animals were observed daily, and radio-graphs were taken of the operated radius every two weeks for the first eight weeks and monthly until necropsy at 12 weeks. The rabbits were scheduled to survive for 12 and 24 weeks post-surgery.

At necropsy, the right and left radii were removed and the operated radius was evaluated for gross signs of healing (callus formation and union). The examination included the presence of bone indicating a union or the presence of cartilage, soft tissue or cracks within the defect indicating a possible unstable union.

The radii were then fixed in 10% neutral buffered formalin and processed for histologic and morphometric evaluations.

Radiographs taken at 0, 2, 4, 6, 8, and 12 weeks indicated a robust healing response as early as two weeks and the defect sites continue to improve and remodel towards reconstituting the natural cortices of the radius. The progressive healing observed was consistent between the calcium phosphate collagen matrix treated groups and the autografts control group. There was little difference in radiographic unions between the two cross-lining groups.

In earlier studies, it had been shown that defects left empty or untreated (negative control) contained little or no new bone. In this test the autograft (positive control) formed a stable boney union. The calcium phosphate collagen treated defects which included bone marrow also demonstrated steady bridging with new bone comparable to that seen with autograft.

Example III (Comparative Example)

A batch of calcium phosphate mineral was prepared without the addition of collagen. The mineral was harvested, washed, and lyophilized to a dry powder. Infrared spectroscopy showed it to be hydroxyapatite in character.

An admix matrix was made by mixing insoluble fibrillar collagen fibers with soluble collagen in a 9/1 weight ratio, at a total solids of 4 wt %. The slurry was mixed by hand and the free mineral was added to make up 25 wt % of the total solids. The slurry was poured into 2 inch square Teflon molds to a depth of approximately 5 mm, frozen at −80 degrees C., and lyophilized. The dry matrix was cross-linked using glutaraldehyde for 30 minutes, washed, and re-lyophilized. The resultant matrix was about 4 mm in thickness, and punch samples of 8 mm diameter were made from the matrix for implantation. For comparison, a recently made batch of mineralized collagen (immobilized mineral), with an ash content of 28 wt % was used for 8 mm diameter punched implants.

The implants were placed subcutaneously in the thoracic fascia, with two implant materials of the same type bilaterally in four rats at each implantation time point of 3, 7, and 14 days. At necropsy, the implants were scored for tissue reaction, and tissue blocks taken for histology. H&E stained sections of the implant and surrounding tissue were examined for each animal at each time point to characterize tissue reaction and integration.

| | OBSERVATIONS AT NECROPSY | |
|---|---|---|
| | Admix (non-immobilized mineral) | Mineralized collagen |
| 3 days | Surrounding tissue clear, implants mushy | Surrounding tissue clear, implants soft |
| 7 days | Surrounding tissue clear, implants soft, but feel thickened | Surrounding tissue clear, implants soft to firm |
| 14 days | Surrounding tissue inflamed, implants firm but feel thickened | Surrounding tissue clear, implants firm |

The clinical observations at necropsy indicate a much greater inflammatory response and degradative effect on the admix formulation as compared to the immobilized mineralized collagen in the rat subcutaneous implant model. Observations describe a mushy implant at three days. At seven and 14 days, a thickened implant is observed, probably due to the dramatic fibrous capsule response of the admix formulation as observed histologically. The formulation with immobilized mineral in comparison demonstrated clear surrounding tissue and normal implant appearance at all three time points.

Histologic examination showed that the admix formulation resulted in a high level of both acute and chronic inflammation as demonstrated by the late (14 day) PMN activity and early (3 day) giant cell activity. The giant cells indicate that phagocytic activity is being organized probably in response to the large amount of loosely associated particles of mineral. Fibroblastic invasion is still observed and tissue necrosis was not evident.

In contrast, the formulation with mineral particles immobilized on the collagen fibers demonstrates a more typical implant-tissue reaction. At the three day time point, acute inflammation is observed which rapidly subsides to a more chronic implant reaction at seven days, with only moderate inflammation while fibroblastic invasion and neovascularization is occurring at the implant periphery. At 14 days, signs of increased inflammation are visible, perhaps indicative of additional mineral release from the collagen fibers due to collagen degradation.

The admix formulation of the collagen and hydroxyapatite mineral components demonstrates a significant acute inflammatory response in subcutaneous rat implants. The immobilization of the mineral component in the mineralized collagen composition appears to reduce the bioavailability of the mineral, reducing inflammation while continuing to support tissue integration during wound healing.

Example IV

Implantation in Soft Tissue Sites

The mineralized collagen matrix according to the invention was implanted into the subcutaneous tissue of 5 to 6 week old male Sprague Dawley rats and evaluated by histological methods after 4 and 8 weeks. After 4 weeks, the ingrowth of fibrous tissue into the ovoid mass of eosinophilic implant was observed. A moderate to marked chronic inflammatory response with a lymphocytic infiltrate was also observed. Peripherally, dense fibrous tissue and multinucleate giant cells were present. A moderate amount of mineralized collagen implant remained at this time point. At 8 weeks, implants of mineralized collagen showed fine and dense fibrous tissue and small void spaces. Moderate inflammation, primarily peripherally, with infiltrates of chronic inflammatory cells and scattered giant multinucleate cells was also observed. Three of six specimens showed small amounts of residual implant material, while the remaining three implant sites contained only traces of implant.

Example V

Residence Time of Implanated Mineralized Collage Matrix

The mineralized collagen matrix according to the invention was combined with autologous bone marrow and implanted into 1.5 cm segmental defects in the radius of New Zealand White rabbits. After 12 weeks, implant sites were evaluated histologically and showed residual mineralized collagen matrix present and in close apposition to the bony matrix.

Example VI

Release of MP52

The mineralized collagen matrix according to the invention was hydrated with Morphogenic protein-52 (MP52) at a concentration of 0.1 mg MP52/cc matrix. The hydrated matrix was lyophilized. The lyophilized matrix was placed in PBS at 37° C. and the release of MP52 from the matrix was measured. At the following timepoints—15 min, 30 min, 1 hr and 18 hr, the cumulative release was 5%, 7%, 9% and 10% respectively. 90% of the loaded MP52 was recovered from the matrix after 18 hr.

Example VII

Release of Antibiotics

The mineralized collagen matrix according to the invention was hydrated with vancomycin at a concentration of 10 mg of vancomycin/cc matrix. The hydrated matrix was lyophilized. The lyophilized matrix was placed in PBS at 37° C. and the release of vancomycin from the matrix was measured. At the following timepoints—6 hr, 24 hr, 51 hr, 73 hr and 97 hr, the cumulative release was 40%, 63%, 72%, 80% and 83% respectively.

Example VIII

Shape Memory

The mineralized collagen matrix according to the invention can be easily hydrated by placing the matrix in fluid. The matrix maintains its integrity and shape after hydration. The hydrated matrix can be compressed and manually inserted through a narrow opening but returns to its original size and shape on rehydration. During the manipulation and compression the matrix maintains its integrity without any substantial loss of fibers.

What is claimed is:

1. An implantable porous, biodegradable, three-dimensionally fixed matrix having shape memory comprising a network of water-insoluble mineralized biopolymer fibers, and a water-soluble binder which is adhered to said fibers and rendered insoluble in the matrix by cross-linking;
   wherein said mineralized biopolymer fibers are mineralized by precipitating calcium and phosphate ions in the presence of said biopolymer fibers, and said mineralized biopolymer fibers are immobilized within said matrix by said water-soluble binder; and
   wherein said matrix is compressible from an initial size, shape and porosity to a compressed state and returns from said compressed state to said initial size, shape and porosity without substantial loss of said fibers or binder.

2. An implantable, porous, biodegradable, three-dimensionally fixed matrix for bone growth having shape memory which maintains its porosity for a period greater than about fourteen days after implantation into a physiological environment in which said bone growth is required, comprising insoluble mineralized biopolymer fibers and a water-soluble binder which is adhered to said fibers and rendered insoluble in the matrix by cross-linking;
   wherein said mineralized biopolymer fibers are mineralized by precipitating calcium and phosphate ions in the presence of said biopolymer fibers, and said mineralized biopolymer fibers are immobilized within said matrix by said water-soluble binder; and
   wherein said matrix is compressible from an initial size, shape and porosity to a compressed state and returns from said compressed state to said initial size, shape and porosity without substantial loss of said fibers or binder.

3. A matrix according to claim 1 or 2 further comprising an additive.

4. A matrix according to claim 3 wherein said additive comprises a drug.

5. A matrix according to claim 4 wherein said drug comprises an antibiotic.

6. A matrix according to claim 4 further comprising a growth factor.

7. A matrix according to claim 4 further comprising marrow.

8. A matrix according to claim 4 wherein said mineralized biopolymer fibers are in the form of mineralized collagen containing about 30-95% by weight of collagen.

9. A matrix according to claim 1 or 2 wherein said water-soluble binder is selected from the group consisting of soluble collagen, gelatin, polylactic acid, polyglycolic acid, copolymers of lactic and glycolic acid, polycaprolactone, carboxymethylcellulose, cellulose esters, dextrose, dextran, chitosan, hyaluronic acid, ficol, chondroitin sulfate, polyvinyl alcohol, polyacrylic acid, polypropylene glycol, polyethylene glycol, water soluble polyacrylates and water soluble polymethacrylates.

10. A matrix according to claim 1 or 2 wherein said biopolymer comprises fibrillar collagen.

11. A matrix according to claim 1 or 2 wherein said mineral comprises hydroxyapatite.

12. A matrix according to claim 2 wherein said mineral is released into said physiological environment during replacement with bone in a time-release profile which maintains said porosity for said period of time.

13. A matrix according to claim 1 or 2 further comprising marrow cells.

14. A matrix according to claim 1 or 2 further comprising autogenous bone.

* * * * *